(12) United States Patent
Webster

(10) Patent No.: US 9,814,300 B2
(45) Date of Patent: Nov. 14, 2017

(54) CLIP-ON EARPLUG CASE

(76) Inventor: Monty James Webster, Godfrey, IL (US)

(*) Notice: Subject to any disclaimer, the term of this patent is extended or adjusted under 35 U.S.C. 154(b) by 0 days.

(21) Appl. No.: 13/289,784

(22) Filed: Nov. 4, 2011

(65) Prior Publication Data

US 2012/0132556 A1 May 31, 2012

Related U.S. Application Data

(60) Provisional application No. 61/417,977, filed on Nov. 30, 2010.

(51) Int. Cl.
*A61B 19/02* (2006.01)
*A45F 5/02* (2006.01)
*A45C 11/00* (2006.01)
*A61F 11/08* (2006.01)

(52) U.S. Cl.
CPC ............. *A45F 5/02* (2013.01); *A45C 11/00* (2013.01); *A45C 2011/007* (2013.01); *A61F 11/08* (2013.01)

(58) Field of Classification Search
CPC . A61B 19/02; A61B 2019/0202; A45F 5/021; A45F 5/02; A01K 27/005; F16B 21/186; A61F 11/10; B65D 15/04; B65D 25/005; B65D 5/16; B65D 1/16; B65D 2585/545; A45C 11/00
USPC .... 24/3.11, 3.7, 600.7, 600.8; 224/668, 671, 224/679, 268, 269, 255, 199; 206/438, 206/284, 815, 231, 83, 6, 294, 5.1; D3/212, 264, 263, 279; 150/110, 152
See application file for complete search history.

(56) References Cited

U.S. PATENT DOCUMENTS

| | | | | |
|---|---|---|---|---|
| 898,789 | A * | 9/1908 | Schleicher | 59/95 |
| 1,122,941 | A * | 12/1914 | Kameras et al. | A44C 25/004 63/19 |
| 1,715,348 | A * | 6/1929 | Barbara | A45C 11/329 150/900 |
| 2,491,310 | A * | 12/1949 | Heimann | 411/518 |
| 3,085,584 | A * | 4/1963 | Hollinger | 134/137 |
| 3,435,997 | A * | 4/1969 | Johnston | 222/400.7 |
| 4,049,165 | A * | 9/1977 | Goldhaft | 224/236 |
| 4,242,775 | A * | 1/1981 | Eickmann | 24/16 R |
| 4,665,592 | A * | 5/1987 | Kasai | 24/601.2 |
| 4,689,860 | A * | 9/1987 | Suchowski | 24/600.7 |
| 4,697,948 | A * | 10/1987 | Fukuda | 403/71 |
| 4,819,306 | A * | 4/1989 | Kasai | 24/600.7 |
| 4,987,650 | A * | 1/1991 | Eickmann | 24/16 R |
| D320,885 | S * | 10/1991 | Fitzhugh | D3/264 |
| 5,806,678 | A * | 9/1998 | H.ang.kansson | 206/438 |
| 6,286,190 | B1 * | 9/2001 | Friend et al. | 24/265 H |

(Continued)

OTHER PUBLICATIONS farmerssupply.net/browseproducts/Reusable-Ear-plugs-with- case (FarmersSupply web page Aug. 2007).*

*Primary Examiner* — Anthony Stashick
*Assistant Examiner* — James M Van Buskirk
(74) *Attorney, Agent, or Firm* — Grace J. Fishel

(57) ABSTRACT

An earplug container is combined with a reusable clip such as a snap bolt fastener and the clip is rigidly attached to a wall of the container, for example by an E-clip or by integral molding. The resulting clip-on earplug container provides a secure and compact earplug case for attachment to the exterior of clothing of an active user such as a lumberjack or tree trimmer. Other exemplary embodiments are also described.

6 Claims, 2 Drawing Sheets

(56) References Cited

U.S. PATENT DOCUMENTS

| | | | |
|---|---|---|---|
| 6,530,345 B2 * | 3/2003 | Donze | 119/774 |
| 6,739,022 B1 * | 5/2004 | Chen | 24/598.1 |
| 6,948,218 B1 * | 9/2005 | Donze | 24/265 H |
| 6,973,812 B2 * | 12/2005 | Piermattei | 70/456 R |

* cited by examiner

CLIP-ON EARPLUG CASE

CROSS-REFERENCE TO RELATED APPLICATIONS

This is a non-provisional of U.S. Provisional Utility Patent Application Ser. No. 61/417,977 filed Nov. 30, 2010.

BACKGROUND

Field

This invention relates generally to special receptacles (class 206), specifically to special receptacles for body treatment devices (subclass 363), and more specifically to special earplug receptacles.

Prior Art

Earplug containers are typically plastic containers with smooth exteriors so that they can be easily inserted into a pocket and easily removed from the pocket without catching on loose threads or a pocket lining. Projections get in the way of doing that. For some occupations where ear plugs are more frequently needed, such as factory work, it is desirable to have the earplug more accessible, so they are connected by a string and worn around the neck or attached by a cord or chain to some clip that can be attached to a clothing flap or loop. For more active occupations, such as a lumberjack or motorcyclist that is not secure enough so a closed clip such as a carabiner or snap bolt is added to the chain. These chain-mounted closed clips tend to flop around and get in the way of the user until they catch on something and get pulled loose or rip the clothing.

SUMMARY

The above noted problems are solved by the exemplary embodiments disclosed below. In a first "best mode" exemplary embodiment, a snap bolt is rigidly attached to a wall of the ear plug container by an E-clip. The first exemplary embodiment provides a secure and compact earplug case for attachment to the exterior of clothing of an active user such as a lumberjack or tree trimmer. Other exemplary embodiments are also described and the invention is applicable to containers for storage of small objects other than earplugs.

DRAWINGS

The invention will be better understood by referring to the attached drawing showing exemplary embodiments.

Figure 1:
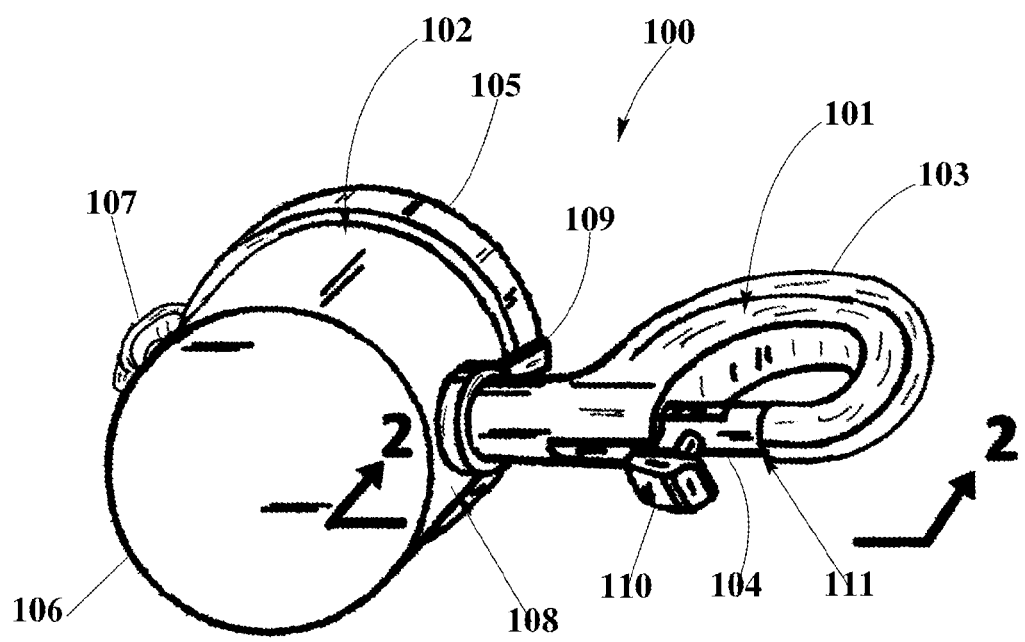
Figure 2:
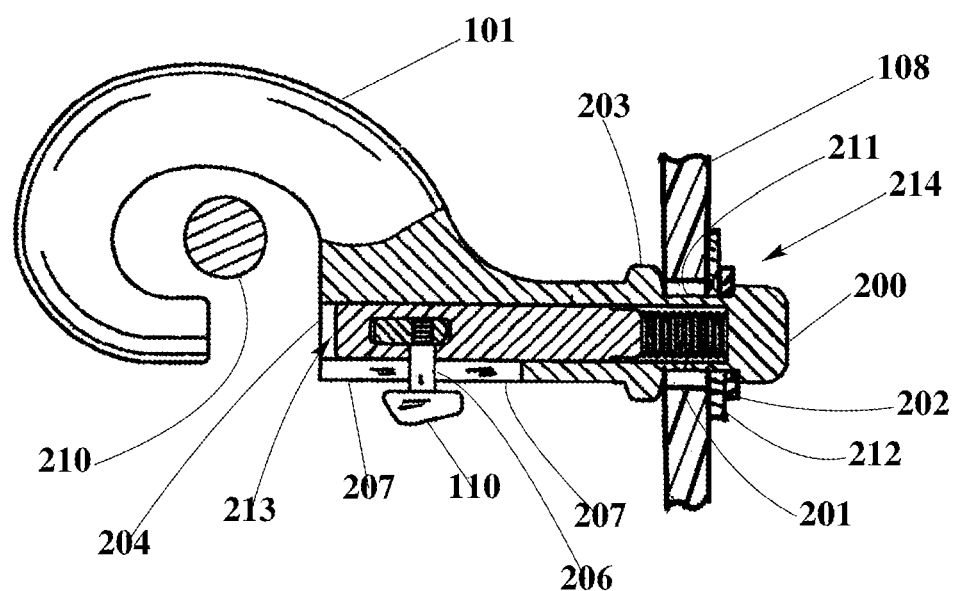

FIG. 1 is a bottom side perspective view of a first exemplary embodiment 100 in a closed position; and FIG. 2 is a cross sectional view of embodiment 100 along lines 2-2 of FIG. 1.

DETAILED DESCRIPTION

First Exemplary "Best Mode" Embodiment

FIG. 1 is a bottom side perspective view of a first exemplary embodiment 100 in a closed position. First exemplary embodiment 100 is an attachable earplug receptacle comprising a chrome-plated metal snap bolt clip 101 and a plastic canister 102. Clip 101 has a metal J-shaped main body portion 103 and a metal closure bolt 104 with a tab 110. Bolt 104 is spring-biased toward a closed position 111 as shown, but can be opened to an open position 213 (see FIG. 2) by pressing tab 110 to the left. Canister 102 comprises a plastic lid 105 connected to a plastic cup-like bottom portion 106 by a flexible plastic hinge 107 and resilient plastic snap closure tab 109, and is configured so as to receive and securely contain a pair of earplugs (not shown). Clip 101 is attached to a wall 108 of canister 102 in the manner shown in FIG. 2. Tab 109 is aligned with clip 101 while hinge 107 is oriented 180 degrees from clip 101, so that lid 105 opens downwardly (to the left in FIG. 1) to form a shelf and assist in preventing the contents of canister 102 from falling. Clip 101 is hung from any loop or opening on a jacket and thus in FIG. 1, right is up and left is down and the canister 102 would hang from clip 101. Lid 105 is opened by pulling outwardly (up in FIG. 1) on tab 109 and rotating lid 105 counterclockwise about hinge 107 to gain access to the earplugs (not shown) in canister 102.

FIG. 2 is an inverted (up is left and down is right) cross sectional view of embodiment 100 taken along lines 2-2 of FIG. 1, but showing bolt 104 in an open position 213 such that an outerwear ring 210 can pass into position to be captured by bolt 104 when bolt 104 is released to return to a closed position as shown in FIG. 1. FIG. 2 is intended to show both an exemplary construction of clip 101 and an exemplary retainer 214 for attachment of clip 101 to wall 108. Wall 108 has an opening 201 through which an end flange 200 and an annular recess 211 of clip 101 extend. Clip 101 also has a large diameter flange 203 of a greater diameter than that of opening 201 to limit insertion of of end flange 200 and recess 211 through opening 201 into canister 102. A washer 212 and E-shaped snap ring 202 fasten clip 101 to wall 108. Washer 212 has an outer diameter greater than opening 201 and an inner diameter. Ring 202 has an outer diameter greater than the inner diameter of washer 212 and an inner diameter slightly less than the diameter of recess 211 but can be resiliently expanded when pushed to the left over flange 200 so that ring 202 can snap into recess 211 and prevent flange 200 from passing back out of opening 201, thus retaining clip 101 attached to wall 108. Clip 101 also has an internal passageway 204 configured to receive closure bolt 104 and a compressible spiral spring 205. Clip 101 also has a slot 207 through which a stem 206 of tab 110 radially passes to screw into a captive nut 209 within bolt 104.

Second Exemplary Embodiment

A second alternate exemplary embodiment (not shown) would have a metal canister for added strength rather than plastic canister 102, but would otherwise be the same as embodiment 100.

Third Exemplary Embodiment

A third exemplary embodiment (not shown) would have a screw on lid rather than a hinge 107 and locking tab 109 as shown in FIG. 1. The advantage of a hinged lid is that it is not likely to be lost since it is attached. The advantage of a screw on lid is that it is more easy to make the canister waterproof since more pressure can be applied due to the mechanical advantage of a screw. A string, wire or chain (not shown) could be provided to connect the lid to the remainder of the canister to eliminate this problem and a waterproof seal would be needed for opening 201.

Fourth Exemplary Embodiment

A fourth exemplary (not shown) would have a plastic snap bolt clip rather than metal clip 101. The advantage of a plastic clip is that it could be molded integral with the canister rather than having a separate clip and having to fasten that clip to the canister. This integral molding, although not removable and not rotatable like retainer 214 would significantly reduce manufacturing costs as would plastic rather than metal construction. Even for such a plastic clip, spring 205 and closure bolt 104 might still be metal for added strength and durability.

Fifth Exemplary Embodiment

A fifth exemplary embodiment (not shown) would have a carabiner clip (swing gate type clip) rather than snap bolt type metal clip 101, but have the carabiner clip closely attached to opening 201 using a snap ring connection similar to that shown in FIG. 2 rather than to a chain, so the receptacle does not flop around as much. That is, the attachment could be by a projection with a flange 203, recess 211, ring 202 and flange 200 and an opening 201, or some other close fitting attachment. Alternatively, such carabiner clip could have a plastic body integrally molded to the canister, as is the plastic snap bolt clip of the fourth exemplary embodiment above. The advantage of a plastic clip is that it could be molded integral with the canister rather than having a separate clip and having to fasten that clip to the canister. This integral molding would significantly reduce manufacturing costs as would plastic rather than metal construction. Even for such a plastic clip, spring 205 and closure bolt 104 might still be metal for added strength.

Sixth Exemplary Embodiment

A sixth exemplary embodiment (not shown) would have a threaded connection rather than snap ring 202. Snap bolts conventionally come with flanged connections, but for a close fitting connection like this might have a threaded end of a diameter equal to that of recess 211 and no flange 200 so that opening 201 could be made smaller and clip 101 might be more easily attached with a simple washer and nut.

CONCLUSION, RAMIFICATIONS, AND SCOPE

Accordingly the reader will see that, according to the invention, I have provided for a more compact and secure earplug receptacle for those applications where it is desired to attach the receptacle to outerwear and make it readily available for use.

While the above description contains many specificities, these should not be construed as limitations on the scope of the invention, but in accordance with the principles set forth by the US Court of Appeals for the Federal Circuit in *Phillips v. AWH Corporation,* 415 F.3d 1303 (CAFC 2005), are exemplifications of the presently preferred embodiments thereof intended to meet enablement and best mode requirements of 35 USC 112. The person having ordinary skill in the art will recognize that many other ramifications and variations are possible within the scope of the invention. Thus the scope of the invention and claim construction should be determined broadly by the appended claims and their legal equivalents in view of both intrinsic and extrinsic evidence as to the person having ordinary skill in the art and the broad scope such a person would comprehend consistent with such limitations as are needed to define patentably from the prior art, and not limited to just one or more of the examples given.

What is claimed is:

1. An earplug case, comprising: a case body having a side with an aperture in said side and a hinge with a hinged lid oriented 180 degrees from said aperture on the case body, a snap-bolt clip disposed in a position having a post extending through said aperture, and a retainer for retaining said post in said position so as to maintain said clip attached to said case,
   whereby the hinged lid provides a shelf to assist in preventing earplugs stored in the case from falling when the lid is hinged open and the case is hung by the snap-bolt clip.

2. The case of claim 1, wherein said retainer is a snap ring engaging the post of the snap-bolt clip within said case body.

3. The case of claim 1, wherein the case is plastic and said post is plastic.

4. The case of claim 2, wherein said post has a flange to limit insertion of the post into the aperture and an end flange with an annular recess, said snap ring engaging the post in the annular recess.

5. The case of claim 1, wherein said case is configured for storage of a pair of earplugs.

6. The case of claim 1, wherein said case is configured for storage of small items.

* * * * *